(12) United States Patent
Dmuschewsky

(10) Patent No.: US 10,813,674 B2
(45) Date of Patent: Oct. 27, 2020

(54) FASTENING ELEMENT FOR PREVENTING UNWANTED RELEASE OF A CONNECTION, SET CONSISTING OF FASTENING ELEMENT AND COUNTER-PIECE, AND USE OF THE FASTENING ELEMENT

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 16/073,625

(22) PCT Filed: Feb. 1, 2017

(86) PCT No.: PCT/EP2017/052116
§ 371 (c)(1),
(2) Date: Jul. 27, 2018

(87) PCT Pub. No.: WO2017/140497
PCT Pub. Date: Aug. 24, 2017

(65) Prior Publication Data
US 2019/0000519 A1    Jan. 3, 2019

(30) Foreign Application Priority Data

Feb. 18, 2016   (EP) .................................... 16156328

(51) Int. Cl.
*A61B 17/86* (2006.01)
*F16B 35/06* (2006.01)
(Continued)

(52) U.S. Cl.
CPC ...... *A61B 17/8605* (2013.01); *A61B 17/8047* (2013.01); *A61B 17/8052* (2013.01);
(Continued)

(58) Field of Classification Search
CPC ............ A61B 17/8605; A61B 17/7266; A61B 17/7291; A61B 17/8014; A61B 17/8047;
(Continued)

(56) References Cited

U.S. PATENT DOCUMENTS 7,955,362 B2 *  6/2011  Erickson ............ A61B 17/8052
                                              606/280
7,963,982 B2 *  6/2011  Kirschman ........ A61B 17/8052
                                              606/291
(Continued)

FOREIGN PATENT DOCUMENTS

CN    101943201 A    1/2011
CN    101960158 A    1/2011
(Continued)

OTHER PUBLICATIONS

PCT International Search Report for application PCT/EP2017/052116, dated Apr. 24 2017 (15 pages).
(Continued)

*Primary Examiner* — Zade Coley
(74) *Attorney, Agent, or Firm* — Joseph V. Saphia; Haug Partners LLP

(57) ABSTRACT

The invention relates to a fastening element for preventing unwanted release of a connection between the fastening element and a counter-piece. The fastening element is designed to come into engagement with the counter-piece through a rotary movement of the fastening element about an axis of rotation in a connection direction. Such fastening elements are suitable for use in a wide range of technical fields, for example the automotive industry, household electronics and medical technology, in particular in the field of instruments for implants or prostheses and modular systems of implants or prostheses.

19 Claims, 2 Drawing Sheets

(51) Int. Cl.
*F16B 39/284* (2006.01)
*F16B 39/32* (2006.01)
*A61B 17/80* (2006.01)
*A61B 17/00* (2006.01)

(52) U.S. Cl.
CPC .......... *F16B 35/06* (2013.01); *F16B 39/284* (2013.01); *F16B 39/32* (2013.01); *A61B 2017/00862* (2013.01)

(58) Field of Classification Search
CPC ....... A61B 17/8052; A61B 17/86–8695; F16B 35/06; F16B 39/284; F16B 39/32; F16B 23/0061; F16B 35/04
See application file for complete search history.

(56) References Cited

U.S. PATENT DOCUMENTS

| | | | | |
|---|---|---|---|---|
| 8,728,130 B2* | 5/2014 | Kirschman | ........ | A61B 17/8052 606/291 |
| 10,076,369 B2* | 9/2018 | Chin | .................. | A61B 17/8052 |
| 2004/0127896 A1* | 7/2004 | Lombardo | ......... | A61B 17/8615 606/290 |
| 2008/0097444 A1* | 4/2008 | Erickson | ............ | A61B 17/8052 606/281 |
| 2009/0024170 A1* | 1/2009 | Kirschman | ........ | A61B 17/8052 606/280 |
| 2009/0192549 A1 | 7/2009 | Sanders et al. | | |
| 2011/0082506 A1* | 4/2011 | Lore | .................. | A61B 17/8052 606/279 |
| 2011/0160776 A1* | 6/2011 | Erickson | ............ | A61B 17/8052 606/286 |
| 2013/0184749 A1* | 7/2013 | Lore | .................... | A61B 17/888 606/246 |
| 2015/0216573 A1* | 8/2015 | Chin | .................. | A61B 17/8047 606/279 |

FOREIGN PATENT DOCUMENTS

| | | |
|---|---|---|
| EP | 1 032 767 A2 | 6/2000 |
| WO | 2009001421 A1 | 12/2008 |
| WO | 2009012195 A1 | 1/2009 |

OTHER PUBLICATIONS

European Search Report for application EP 16 15 6328.3, dated Aug. 29, 2016 (8 pages).

Office Action issued in the corresponding Chinese Patent Application No. CN 201780012007.7 dated Feb. 3, 2020 and its English Translation.

* cited by examiner

FASTENING ELEMENT FOR PREVENTING UNWANTED RELEASE OF A CONNECTION, SET CONSISTING OF FASTENING ELEMENT AND COUNTER-PIECE, AND USE OF THE FASTENING ELEMENT

CROSS REFERENCE TO RELATED APPLICATIONS

This application is a National Stage of International Application No. PCT/EP2017/052116 filed on Feb. 1, 2017. The contents of the above document are incorporated herein by reference in its entirety.

BACKGROUND

Fastening elements are well-known. However, increasingly high demands are being placed on fastening elements to the effect that there should be no unwanted release of the fastening element once the connection between the fastening element and the counter-piece has been made. In particular, no reliable fastening elements are known which reliably prevent unwanted release even under vibration or alternating loads.

SUMMARY

The object of the present invention is to design a fastening element or a set comprising a fastening element and a counter-piece or a use of a fastening element with a simple construction in such a manner that unwanted release of the connection between the fastening element and the counter-piece can be reliably prevented.

This object is achieved according to the invention by the fastening element with the features of claim 1. As a result, a fastening element for preventing unwanted release of a connection between the fastening element and a counter-piece is provided, the fastening element being designed to come into engagement with the counter-piece through a rotary movement of the fastening element about an axis of rotation in a connection direction. The fastening element has an elastic element, in particular a spring element, with a contact portion for making contact with the counter-piece, the elastic element being designed such that it can be arranged, in a prestressed and/or non-prestressed state, at least in certain portions at an angle to a radial, with respect to the axis of rotation, in a plane perpendicular to the axis of rotation.

In addition, according to claim 13, a set of the fastening element according to the invention and the counter-piece is provided, the fastening element and the counter-piece being designed in such a manner that, at least in the connected state of the fastening element and the counter-piece, the contact portion makes contact with the counter-piece at a contact point and that a tangent, with respect to the axis of rotation, at the contact point extends at least to one portion of the elastic element at an angle not equal to 90° in a plane perpendicular to the axis of rotation.

According to claim 16, the use of a fastening element for preventing unwanted release of a connection between the fastening element and a counter-piece is provided, the fastening element being designed to come into engagement with the counter-piece through a rotary movement of the fastening element about an axis of rotation in a connection direction, the fastening element having an elastic element, in particular a spring element, with a contact portion for making contact with the counter-piece at a contact point, and the contact portion making contact with the counter-piece in the connected state of the fastening element and the counter-piece, and the elastic element in the connected state being arranged in such a manner that a tangent, with respect to the axis of rotation, at the contact point extends at least to one portion of the elastic element at an angle not equal to 90° in a plane perpendicular to the axis of rotation.

According to claim 17, the use of the fastening element or set according to the invention is provided for connecting implant components, in particular an (angularly stable) bone plate.

The radial is understood to mean a straight line which extends radially away from the axis of rotation in a plane perpendicular to the axis of rotation.

In particular, the connected state is understood to be the state in which the fastening element is in engagement with the counter-piece in such a manner that the engagement portion of the fastening element and the engagement portion of the counter-piece are completely accommodated in one another and the non-positive connection is achieved in the process.

The elastic element can be designed integrally with the fastening element or it can be arranged separately on the fastening element. The region of the counter-piece which comes into engagement with the fastening element can be integral to or separate from the region of the counter-piece with which the contact portion of the fastening element comes into contact. For example, a first and second counter-piece can be provided, the first counter-piece serving to engage with the fastening element through the rotary movement (by having a thread, for example) and the second counter-piece serving to contact with the elastic element. It is conceivable that an element to be fastened is provided between the first and second counter-piece, said element being fastened to the counter-piece by the connection between the fastening element and the counter-piece. It is also possible that the fastening element is connected to the counter-piece and at the same time locks a further object, in that the fastening element engages in the further object through the counter-piece and thus prevents the object from being removed from the counter-piece.

The counter-piece can consist of two separate portions. One portion of the counter-piece can be connected or fastened to the other portion of the counter-piece using the fastening element. In other words, the counter-piece can also be partially formed in the object to be fastened or can be provided in addition to the object to be fastened.

Due to the fact that the elastic element is arranged at an angle to the radial and respectively at an angle not equal to 90° relative to a tangent in the contact point, the radial forces are different when rotating the fastening element in the connection direction and in a direction contrary to the connection direction.

The invention is based on the idea of preventing the unwanted release of a fastening element from a counter-piece in that at least the initial release of the connection between the fastening element and the counter-piece requires a greatly increased application of force which is greater than the additional force which has to be applied because of the elastic element when creating the connection between said fastening element and said counter-piece. As the necessary force during the at least initial release is increased, it is possible to prevent the occurrence of an unwanted release of the connection between the fastening element and the counter-piece. This increases the reliability of the connection. Due to this increased additional force required to initially release the connection between the fastening element and the counter-piece, the fastening element can be secured against release from the connection with the counter-piece even in the event of vibrations or alternating loads. Thus an object which is connected to the counter-piece or is fastened to it by the connection between the fastening element and the counter-piece is secured against release from the connection with the counter-piece.

In other words, when creating the connection between the fastening element and the counter-piece, the fastening element can be brought into engagement with the counter-piece substantially without additional force, whereas at least on initially rotating the fastening element in the direction contrary to the connection direction such a high force is necessary that this substantially equates to locking the fastening element.

Especially advantageous developments of the invention are disclosed in the dependent claims and in the following. The counter-piece preferably comprises an implant component. It is conceivable that a portion of the counter-piece (for engagement with the fastening element) corresponds to a bone to which a bone plate is to be fastened. The bone plate can comprise a further portion of the counter-piece (for contact with the elastic element). It is also conceivable that the further portion of the counter-piece is provided separately from the bone plate.

In particular, the elastic element is designed such that, due to the contact of the elastic element with the counter-piece, the force which is necessary for engagement with the counter-piece when creating the connection is only slightly increased or is essentially hardly increased, and is designed in such a manner that the force which is necessary between the fastening element and the counter-piece for releasing the connection is greatly increased by the contact of the elastic element with the counter-piece.

The elastic element is preferably designed such that once the increased force has been applied during initial release of the connection, the fastening element can be released from the counter-piece, with only slight or essentially no additional force being needed.

The elastic element is preferably a spring element and is designed such that prestressing can be applied to the elastic element in such a manner that contact can be ensured between the contact portion and the counter-piece at a contact point. By prestressing the elastic element, it is possible to ensure that the restoring forces press the elastic element sufficiently against the counter-piece so that the contact between the contact portion and the counter-piece can be ensured at the contact point.

Further preferably, the elastic element, preferably also in a non-prestressed state, is arranged at an angle to a radial in a plane perpendicular to the axis of rotation in such a manner that, at least at the contact point, the angle between the elastic element and the radial in the connection direction is greater than 0° and less than 90°. In other words, when the connection direction is clockwise, the angle between the elastic element at the contact point towards the radial in the clockwise direction is greater than 0° and smaller than 90°. In contrast, the angle between the elastic element and the radial in the direction contrary to the connection direction, that is the anti-clockwise direction, is more than 270°. It is therefore possible that, due to the elastic element, the additional force to be applied on rotating the fastening element in the connection direction is less than the additional force when rotating the fastening element in the direction contrary to the connection direction.

The angle between the elastic element and the radial in the connection direction is preferably between 5° and 90°, further preferably between 5° and 85°, more preferably between 5° and 45°.

Material and surface of the elastic element and the counter-piece are preferably selected such that the elastic element has a suitable elasticity and/or surface roughness at least in the contact portion with the counter-piece to support a non-positive connection to the counter-piece. The material must not promote sliding friction and in particular has elastic, resilient properties. Preferred surface roughnesses of the elastic element and the counter-piece in their contact region are $R_a$=0.005-25 μm. The material of the elastic element and/or the counter-piece is preferably plastic or metal. Further preferred examples are steels (hardened or unhardened), titanium alloys, cobalt-chrome, brass, bronze, aluminum alloys and various plastics (which have resilient properties), such as PEEK (polyether ether ketone; available, for example, as Zeniva® from Solvay), Radel® (a polyphenylsulfone polymer from Solvay) and Propylux® (a polypropylene plastic from the Westlake Plastics Company). The use of wood or rubber is also conceivable. In principle, a plurality of combinations or material pairings are possible depending on the field of application.

Preferably, the angle in the connection direction between the tangent, in relation to the axis of rotation, at the contact point and at least one portion of the elastic element in a plane perpendicular to the axis of rotation is between 5° and 85°, preferably between 45° and 85°.

Preferably, the elastic element is designed such that a transmission of force to the elastic element on rotating the fastening element about the axis of rotation in the connection direction is smaller than when rotating the fastening element in the direction contrary to the connection direction. This means that, when rotating the fastening element in the connection direction, the elastic element requires less additional application of force as, for example, it is only necessary to overcome a low sliding friction force because the elastic element deforms in a correspondingly yielding manner. In contrast, when rotating the fastening element in the direction contrary to the connection direction, due to the rotation of the fastening element in the direction contrary to the connection direction, force is transmitted to the elastic element in such a manner that said elastic element substantially stiffens and is therefore less elastic so that the friction force occurring at the contact point between the counter-piece and the contact portion is substantially higher than the sliding friction force to be applied when rotating in the connection direction, preferably so high that static friction occurs.

The direction in which the elastic element can be prestressed is preferably different to a direction in which the force can be transmitted to the elastic element on rotating the fastening element. Further preferably, the direction in which the element can be prestressed is perpendicular to the direction in which the force can be transmitted to the elastic element; as a result, the transmission of force and therefore stiffening of the elastic element can be maximized which greatly increases the additional force on initially releasing the connection and therefore prevents unwanted release more reliably.

The elastic element can be designed such that the contact portion of the prestressed elastic element and the counter-piece can be connected non-positively, at least during initial rotation of the fastening element in the direction contrary to the connection direction. In other words, a frictional or non-positive connection should exist between the contact portion and the counter-piece, which comes about due to the radial force acting between the contact portion and the counter-piece. This is to be seen in contrast to a positive connection.

The elastic element is preferably substantially elongated, in particular is designed as a leg, further particularly as a flexible spring. In this embodiment, it is particularly easy to implement the transmission of force and therefore the unwanted release.

The elastic element may comprise metal.

It can have a length of at least 3 mm, preferably of at least 10 mm and/or less than 20 mm.

The fastening element has an engagement portion for engaging with the counter-piece, said engagement portion having at one end an end portion that is preferably circular at least in certain portions, on which the elastic element is arranged. If the elastic element is arranged on an end portion of the engagement portion, the contact portion of the elastic element need not be in contact with the counter-piece during the entire process of bringing the fastening element into engagement with the counter-piece but rather the elastic element is in contact with the counter-piece only shortly before completion of the connection or engagement between the elastic element and the counter-piece. Essentially, therefore, engagement of the fastening element with the counter-piece by way of the engagement portion and making contact between the elastic element and the counter-piece can take place in various axial regions of the fastening element or of the counter-piece.

Preferably, the contact portion of the non-prestressed elastic element projects beyond the engagement portion of the fastening element in the radial direction, preferably by at least 1 mm and more preferably by at least 3 mm. The desired contact with the counter-piece can be ensured with such an embodiment of the contact portion.

More preferably, the end portion projects beyond the engagement portion in the radial direction and/or the contact portion of the non-prestressed elastic element projects beyond the end portion in the radial direction. This embodiment executes the advantages according to the invention particularly well.

The end portion preferably comprises at least one cut-out adjacent to the elastic element. Further preferably, the end portion comprises at least two adjacent cut-outs which are separated from each other by the elastic element. The elastic element can extend into the cut-out(s) if it is prestressed. In other words, the cut-out extends at least in a direction from the elastic element in which the elastic element can be prestressed.

If two cut-outs are provided which are separated from each other by the elastic element, the elastic element can be accommodated in the cut-out both on rotation in the connection direction and also during rotation in the direction contrary to the connection direction.

The fastening element can comprise a plurality of elastic elements which are preferably spaced apart evenly from each other.

In particular, the fastening element is designed as a screw, the engagement portion being designed as a thread and the end portion as a screw head.

The end portion or screw head can comprise a portion for the engagement of a fastening tool for generating the rotary movement of the fastening element about the axis of rotation.

The counter-piece is preferably designed such that it comprises a recess for receiving the elastic element at least in certain portions, preferably for also receiving the end portion of the fastening element. If the counter-piece comprises a recess in which the elastic element can be accommodated, this has the advantage that the contact between the contact portion and the counter-piece can be established in a reliable manner. In this case, the counter-piece can be formed integrally; however, it is also conceivable that the portion with the recess is formed separately from the engagement portion on the counter-piece.

The recess and the end portion can each be substantially circular, the radius of the recess can be greater than that of the end portion and the non-prestressed elastic element can project radially beyond the end portion in such a way that the prestressed elastic element is in contact with the recess at least in certain portions.

The depth of the recess can correspond, in the direction of the axis of rotation, substantially to the thickness of the end portion, preferably also to the thickness of the elastic element, in the direction of the axis of rotation. As a result, the desired contact between the fastening element and the counter-piece can be guaranteed.

Further features and advantages of the invention will become even more apparent from the following detailed description.

DETAILED DESCRIPTION OF PREFERRED EMBODIMENTS

A preferred embodiment of the present invention will be described in detail in the following with reference to the associated drawings.

Figure 1:
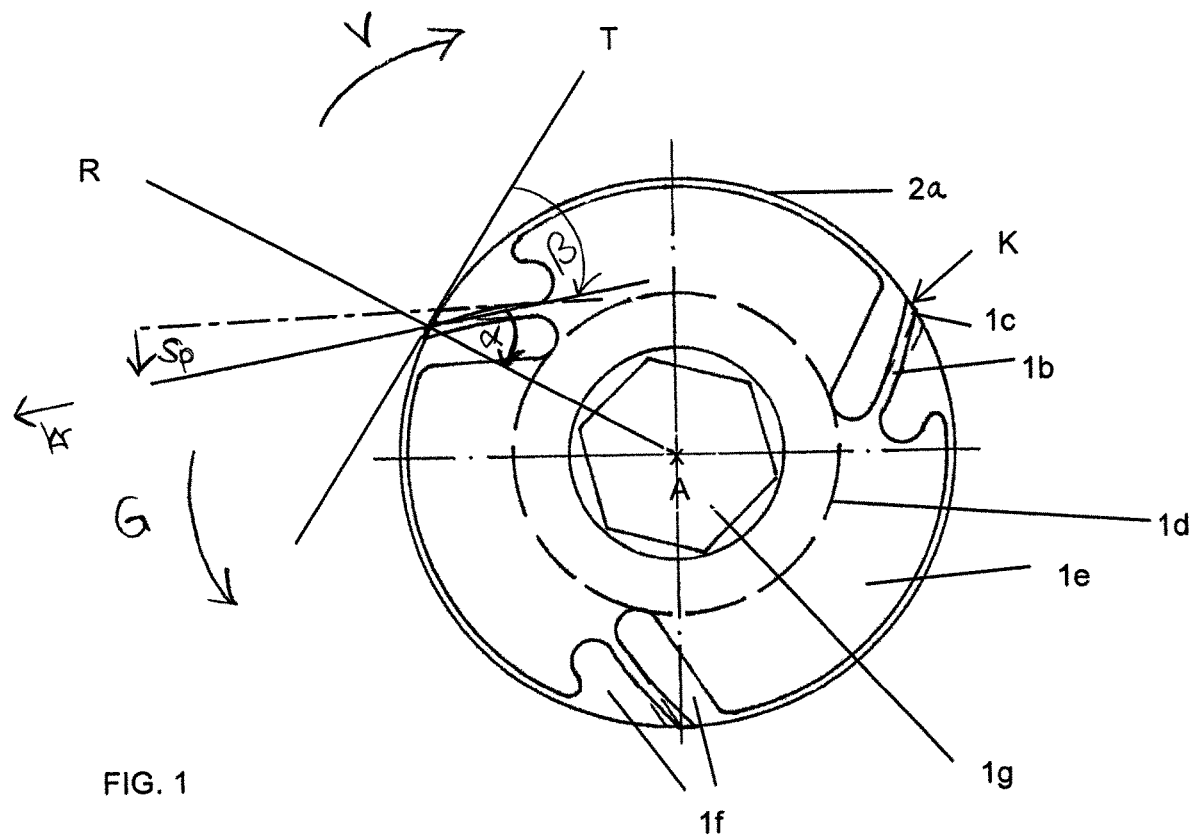
FIG. 1 shows a plan view of a fastening element according to the invention with a counter-piece.

FIG. 1 shows a fastening element 1 for preventing unwanted release of a connection between the fastening element 1 and the counter-piece 2. The counter-piece 2 comprises a recess 2a that is circular, which can also be seen from FIG. 3. The fastening element 1 comprises an elastic element 1b, which can be designed as a spring element, which also has a contact portion 1c for making contact with the counter-piece 2. The elastic element 1b is designed such that it is arranged at least in certain portions at an angle to a radial R, with respect to the axis of rotation A, in a plane perpendicular to the axis of rotation A.

FIG. 1 shows three elastic elements 1b which are arranged evenly distributed from each other with respect to the circumference of the end portion 1e. FIG. 1 shows each elastic element 1b in the prestressed state. The non-prestressed state is indicated by dash lines.

In the embodiment shown in the figures, the elastic element 1b, in both the prestressed and in the non-prestressed state, has a design such that it extends at an angle to a radial R in a plane perpendicular to the axis of rotation A, so that at the contact point K, at which the contact portion 1c makes contact with the counter-piece 2, the angle $\alpha$ between the elastic element 1b and the radial R in the connection direction V meets $0° < \alpha < 90°$. The angle $\alpha$ extends in the clockwise direction from the elastic element 1b to the radial R, as indicated in FIG. 1. This corresponds to the connection direction V, that is to say the clockwise direction.

FIG. 1 also illustrates the angle β at which the elastic element 1b in the connected state in the connection direction V, relative to the tangent T in relation to the axis of rotation A, is arranged at the contact point K in the plane perpendicular to the axis of rotation A, and meets 0°<β<90°. The angle β extends in the connection direction or in the clockwise direction from the tangent T towards the elastic element 1b, as indicated in FIG. 1. The angles α and β together add up to 90°, the angle α preferably being between 5° and 45° and the angle β being between 45° and 85°.

A prestress can be exerted on the elastic element 1b by deflecting it in a direction Sp relative to the non-prestressed state. The direction Sp differs from the direction Kr in which a force can be transmitted to the elastic element 1b on rotating the fastening element 1. The transmission of force to the elastic element 1b on rotating the fastening element 1 about the axis of rotation A in connection direction V is lower (or negligible or zero) than on rotating the fastening element in the direction G contrary to the connection direction.

The elastic element 1b comes with the contact portion 1c into contact with the counter-piece 2 or the recess 2a of the counter-piece. In this case, the elastic element 1b in the prestressed state is arranged in such a manner relative to the counter-piece 2 that the contact portion 1c and the counter-piece 2 can be connected non-positively, at least during initial rotation of the fastening element 1 in the direction G contrary to the connection direction. In other words, the static friction exerted at the contact point K during initial rotation of the fastening element contrary to connection direction V is so high that it cannot be overcome by influences such as vibrations or alternating loads which act on the fastening element or the counter-piece.

The elastic element 1b is elongated, designed as a leg, and has a length of at least 3 mm and less than 20 mm. The elastic element 1b can comprise a metal or consist entirely of metal.

The elastic element 1b is designed as a flexible spring such that the restoring force on the prestressed element acts almost perpendicularly to the longitudinal direction of the elastic element 1b.

In the embodiment shown in the figures, the elastic element 1b is formed integrally with the fastening element 1. However, the elastic element 1b can also be formed separately and can be arranged on the fastening element 1.

Figure 2:
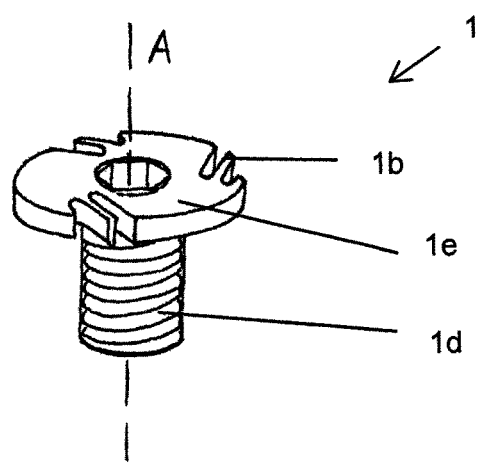
FIG. 2 shows a perspective view of a fastening element according to the invention.

FIG. 2 shows the fastening element 1 which is designed as a screw, the engagement portion 1d, with which the fastening element comes into contact with the counter-piece 2, is designed as a thread. The end portion 1e is designed as a screw head, the engagement portion 1d having at one end the end portion 1e designed as a screw head on which the elastic element 1b is arranged.

The end portion 1e can be circular, as can the recess 2a of the counter-piece 2 not shown in FIG. 2. In the non-prestressed state, the contact portion 1c in the radial direction, which extends from the axis of rotation A in the direction of the radial R can project beyond the engagement portion 1d of the fastening element 1 by at least 1 mm or 5 mm. In this case, the end portion 1e can project beyond the engagement portion 1d in the radial direction R and the contact portion 1c of the non-prestressed elastic element 1b can project beyond the end portion 1e in the radial direction R.

In the embodiment shown in the figures, the end portion 1e comprises two adjacent cut-outs 1f which are separated from each other by the elastic element 1b. The elastic element 1b, if it is prestressed, can extend into one of these opposing cut-outs.

Figure 3:
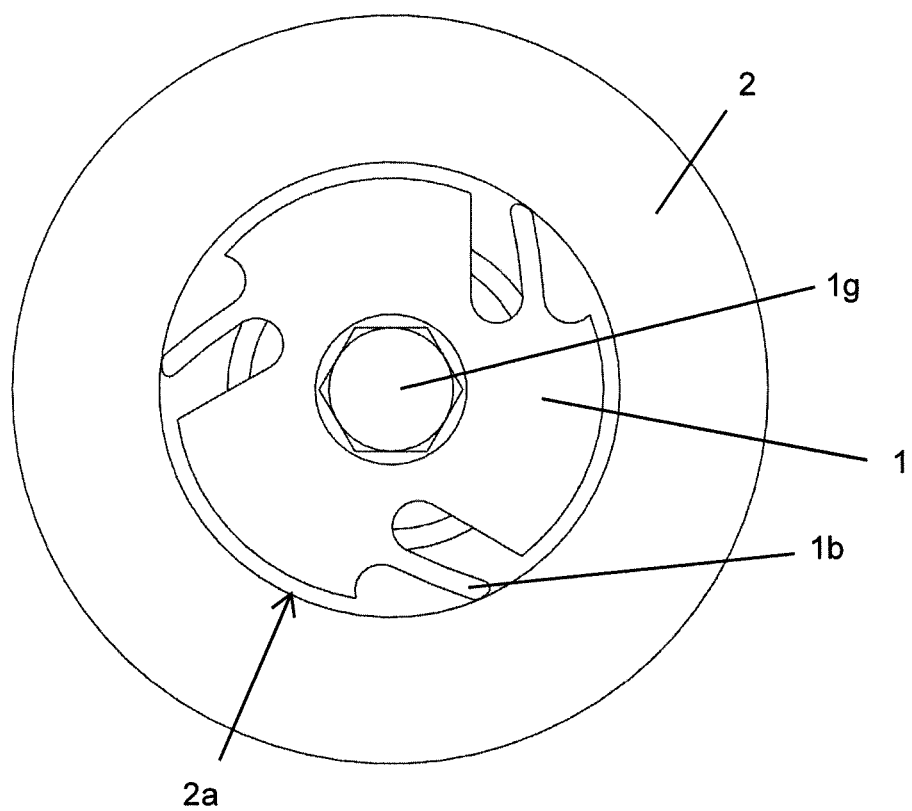
FIG. 3 shows a perspective view of a set according to the invention of a fastening element and a counter-piece.

In addition, the fastening element comprises a portion 1g for the engagement of a fastening tool for generating the rotary movement of the fastening element about the axis of rotation A, as shown in FIGS. 1 and 3.

The recess 2a of the counter-piece 2 is designed such that it can receive the elastic element 1b and the whole end portion 1e. In this case, the radius of the recess 2a is greater than the radius of the end portion 1e and the non-prestressed elastic element which projects radially beyond the end portion 1e is arranged in such a manner that the prestressed elastic element 1b is in contact with the recess 2a at least in certain portions.

The depth of the recess 2a in the direction of the axis of rotation A corresponds substantially to the thickness of the end portion 1e or the elastic element 1b in the direction of the axis of rotation A. Thus the fastening element 1, when it is connected to the counter-piece 2, can be accommodated completely in the recess in the direction of the axis of rotation A without protruding.

The counter-piece 2 can be formed integrally. However, it can also comprise a portion with the recess 2a which is formed separately from the engagement portion of the counter-piece (not shown) such that essentially two separate portions form the counter-piece 2.

The invention claimed is:

1. A set of a fastening element and a counter-piece, the fastening element comprising:
   an elastic element with a contact portion at a circumference of the fastening element for making contact with the counter-piece,
   wherein the elastic element is arranged in the contact portion at an angle to a radial, with respect to the axis of rotation, in a plane perpendicular to the axis of rotation,
   wherein the fastening element is engageable with the counter-piece through a rotary movement of the fastening element about an axis of rotation in a connection direction,
   wherein the fastening element and the counter-piece are designed so that in a connected state of the fastening element and the counter-piece, for preventing an unwanted release of a connection between the fastening element and the counter-piece, the contact portion at the circumference of the fastening element makes contact with the counter-piece at a contact point,
   wherein a tangent, with respect to the axis of rotation, at the contact point extends at least to the contact portion of the elastic element at an angle not equal to 90° in a plane perpendicular to the axis of rotation, which results in a radial force at the contact point when rotating the fastening element in a direction contrary to the connection direction being higher than a radial force at the contact point when rotating the fastening element in the connection direction so that a transmission of force to the elastic element on rotating the fastening element about the axis of rotation in the connection direction is smaller than when rotating the fastening element in the direction contrary to the connection direction.

2. The set according to claim 1, wherein the elastic element is designed such that prestressing can be applied to the elastic element for ensuring contact between the contact portion and the counter-piece at the contact point.

3. The set according to claim 1, wherein the elastic element at the contact point is at an angle α to the radial, wherein the elastic element is oriented radially outwards, with respect to the axis of rotation, in a direction contrary to the connection direction.

4. The set according to claim 3, wherein the angle α between the elastic element and the radial is 0°<α<90°, 5°<α<85°, or 5°<α<45°.

5. The set according to claim 1, wherein the elastic element is designed such that a direction, in which the elastic element can be prestressed, differs from a direction in which the force can be transmitted to the elastic element on rotating the fastening element.

6. The set according to claim 1, wherein the elastic element is designed such that the contact portion of the prestressed elastic element and the counter-piece can be frictionally connected, at least during initial rotation of the fastening element in a direction contrary to the connection direction.

7. The set according to claim 1, wherein the elastic element is substantially elongated.

8. The set according to claim 1, wherein the fastening element has an engagement portion for engaging with the counter-piece, wherein the engagement portion has at one end an end portion, on which the elastic element is arranged.

9. The set according to claim 8, wherein the contact portion of the non-prestressed elastic element projects beyond the engagement portion of the fastening element a direction of the radial.

10. The set according to claim 9, wherein the elastic element projects by at least 1 mm or by at least 3 mm.

11. The set according to claim 8, wherein the end portion projects beyond the engagement portion in a direction of the radial.

12. The set according to claim 8, wherein the end portion has two adjacent cut-outs which are separated from each other by the elastic element, and into which the prestressed elastic element can extend.

13. The set according to claim 8, wherein the contact portion of the non-prestressed elastic element projects beyond the end portion along the radial.

14. The set according to claim 1, wherein the fastening element comprises a plurality of elastic elements.

15. The set according to claim 14, wherein the elastic elements are evenly spaced apart from each other.

16. The set according to claim 1, wherein the counter-piece comprises a recess for receiving the elastic element and an end portion of the fastening element.

17. The set according to claim 16, wherein the recess and the end portion are each substantially circular, the radius of the recess is greater than that of the end portion and the prestressed elastic element is in contact with the recess in the contact portion.

18. The set according to claim 1, wherein the elastic element is designed as a flexible spring.

19. A fastening element according to claim 1, designed as a screw, wherein
the fastening element has an engagement portion that is formed as a thread, and
the fastening element has at one end an end portion that is formed as a screw head.

* * * * *